United States Patent [19]

Bru-Magniez et al.

[11] Patent Number: 5,142,098
[45] Date of Patent: Aug. 25, 1992

[54] METHYLIDENEMALONATE ESTERS DERIVED FROM ESTERS OF 9,10-ENDOETHANO-9,10-DIHYDROAN-THRACANE-11,11-DICARBOXYLIC ACID

[75] Inventors: Nicole Bru-Magniez, Paris; Christian De Cock, Rhode St. Genese; Jacques Poupaert, Ottignies-Louvain La Neuve; Jean-Luc De Keyser, Tervuren; Pierre Dumont, Gembloux, all of France

[73] Assignee: Laboratoires UPSA, France

[21] Appl. No.: 498,103

[22] Filed: Mar. 23, 1990

Related U.S. Application Data

[63] Continuation-in-part of Ser. No. 162,573, Mar. 1, 1988, Pat. No. 4,931,584.

[30] Foreign Application Priority Data

Mar. 5, 1987 [FR] France ................. 87 02991

[51] Int. Cl.⁵ .................. C07C 69/74; C07C 69/593; C07C 57/13
[52] U.S. Cl. .................... 560/80; 560/190; 560/193; 560/197; 560/198; 562/488; 562/595
[58] Field of Search .......... 560/80, 190, 193, 201, 560/197, 198; 562/488, 595; 558/365, 406; 549/513, 559, 265

[56] References Cited

U.S. PATENT DOCUMENTS

| | | | |
|---|---|---|---|
| 2,212,506 | 8/1940 | Bachman | 560/80 |
| 4,013,703 | 3/1977 | Buck | 558/306 |
| 4,139,711 | 2/1979 | Narisada | 560/8 |

FOREIGN PATENT DOCUMENTS 1073917  6/1967  United Kingdom .

OTHER PUBLICATIONS

I *Chemical Abstracts*, vol. 72, No. 22, 111960u, (1970).
II *Chemical Abstracts*, vol. 103, No. 7, 53454c, (1985).

*Primary Examiner*—Jose G. Dees
*Assistant Examiner*—Vera C. Clarke
*Attorney, Agent, or Firm*—Marshall & Melhorn

[57] ABSTRACT

The invention relates to novel monoesters and diesters of 9,10-endoethano-9,10-dihydroanthracene-11,11-dicarboxylic acid.

These novel monoesters and diesters correspond to the following structural chemical formula (II):

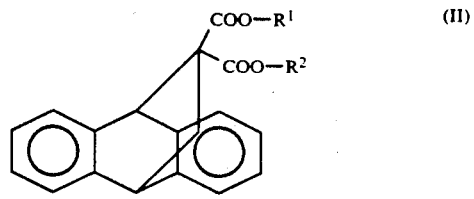

in which $R^1$ and $R^2$ are identical or different and can represent H, an alkali metal or alkaline earth metal atom, a linear or branched alkyl group having from 1 to 6 carbon atoms, an alicyclic group having form 3 to 6 carbon atoms, an alkenyl group having from 2 to 6 carbon atoms, defined in their cis or trans variety, or an alkynyl group having from 2 to 6 carbon atoms, the said groups optionally being substituted by one or more functional groups such as ether, epoxide, halogeno, cyano, ester, aldehyde, ketone, aryl etc., where $R^1$ and $R^2$ cannot be H or ethyl simultaneously. These addition products constitute valuable intermediates for the preparation of methylidenemalonates in high yields and with a high purity.

13 Claims, No Drawings

METHYLIDENEMALONATE ESTERS DERIVED FROM ESTERS OF 9,10-ENDOETHANO-9,10-DIHYDROANTHRA-CANE-11,11-DICARBOXYLIC ACID

This is a continuation-in-part of U.S. patent application Ser. No. 07/162,573 filed on Mar. 1, 1988 by BRUMAGNIEZ et al, now U.S. Pat. No. 4,931,584.

The present invention relates to a process for the preparation of monoesters or diesters of 9,10-endoethano-9,10-dihydroanthracene-11,11-dicarboxylic acid, the novel monoesters or diesters prepared by this process and the use thereof for the preparation of symmetrical or asymmetrical methylidenemalonates.

More particularly, the monoester or diester derivatives according to the invention make it possible to prepare methylidenemalonates of the following formula (I):

$$CH_2=C(COOR^1)(COOR^2) \quad (I)$$

in which $R^1$ and $R^2$ represent linear or branched alkyl groups of 1 to 6 carbon atoms, alicyclic groups having from 3 to 6 carbon atoms, alkenyl groups having from 2 to 6 carbon atoms, defined in their cis or trans variety, or alkynyl groups having from 2 to 6 carbon atoms, the said groups optionally being substituted by functional groups such as ether, epoxide, halogeno, cyano, ester, aldehyde or ketone, aryl etc.

Preferably, the monoester or diester derivatives according to the invention make it possible to prepare methylidenemalonates of the following formula (Ia):

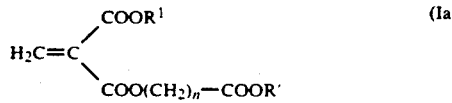

wherein $R^1$ and $R'$ each represents a lower alkyl having from 1 to 5 carbon atoms, and n is an integer from 1 to 5 inclusive.

The methylidenemalonates of formula (Ia) are new compounds synthesized for the first time by the invention process, since the prior art processes were unable to allow the synthesis of them.

The value of the compounds of formula (I) mentioned above is well known both in organic synthesis and in polymer chemistry.

Numerous processes have already been described which make it possible to prepare methylidenemalonates with a formula similar to formula (I) above.

For example, a basic process consists in reacting diethyl malonate with formaldehyde in glacial acetic acid, in the presence of catalysts based on a metal acetate, to produce diethyl methylidenemalonate by distillation, after the catalyst has been filtered off and the solvent has been separated off.

The methylidenemalonate can then be used for polymerization (Chemical Abstracts 1953, vol. 49, abstract 6836d). The same basic reaction is described in Chemical Abstracts, vol. 76, 1972, abstract 139905m. For the polymerization, see "Die Makromolekulare Chemie" 107 (1967), p. 4–5.

However, under the usual conditions of this thermal decomposition of the hydroxyl compound initially formed by the reaction of the malonate with formaldehyde, the above-mentioned methylidenemalonate (I) obtained polymerizes, except in the case where $R^1$ and $R^2$ are represented by the t-butyl group (see P. BALLESTEROS, B. W. ROBERTS and J. WANG, J. Org. Chem. 48, 3603–3605 (1983)).

Furthermore, it has already been proposed to prepare symmetrical or asymmetrical methylidenemalonates by reacting a malonic acid diester with formaldehyde, in the presence of a diene, to give a Diels-Alder addition product, which is then subjected to pyrolysis to give the methylidenemalonate.

Thus, in British Patent Document No. A-1 560 323 to EASTMAN KODAK, the diene used is a linear diene, such as a substituted pentadiene, a hexadiene, isoprene or unsubstituted or substituted buta-1,3-diene, and the intermediate addition product is then pyrolyzed at 600° C. to release the methylidenemalonate.

Moreover, German Patent Document No. C-27 34 082 to PONTICELLO also describes the preparation of asymmetrical methylidenemalonates by carrying out a reaction of the Diels-Alder type between a methyl acrylate and cyclopentadiene to give an intermediate addition product, which is then subjected to various chemical reactions to give a diester before decomposition by pyrolysis to yield the asymmetrical methylidenemalonate diester.

Again, the synthesis of an alkyl alpha-cyanoacrylate by reacting a cyanoacrylic acid ester with a conjugated diene, exemplified by anthracene, is also known; this forms the Diels-Alder addition product, which is then hydrolyzed (see U.S. Pat. No. 3,975,422 or GIRAL, Annal. Pharmaceutiques Francaises 1985, 43, no. 5, pages 439–449, or U.S. Pat. No. 4,056,543 to PONTICELLO): here, however, the cyanoacrylic acid ester initially contains a unit of unsaturation which is used for the addition reaction with the anthracene. This type of addition reaction is very old and had already been described by BACKMAN and TANNER in J. Org. Chem. 4 (1939), p. 500. It has been used to purify previously formed methylidenemalonate by an addition reaction with cyclopentadiene or norbornene (see C.A., vol. 95, 1981, abstract 168570w).

Thus, as far as those skilled in the art are concerned, the use of anthracene has only been described for the formation of an addition product with an unsaturated compound, namely previously formed diethyl methylidenemalonate or a cyanoacrylic acid ester.

Furthermore, the state of the art, in the form of British Patent Document No. A-1, 560 323 mentioned above, teaches those skilled in the art how to use a linear diene to trap the methylidenemalonate in situ during the reaction of a malonate with formaldehyde. Thus, from the point of view of those skilled in the art, this type of trapping process in situ using a cyclic diene did not appear possible, undoubtedly because of the unfavorable reaction conditions.

Now, it has just been discovered, totally unexpectedly and in contradiction to the teaching of the state of the art, that anthracene is a conjugated diene which does make it possible for the methylidenemalonate formed in situ by the reaction of malonate with formaldehyde to be trapped very efficiently (i.e. with excellent yields) and very simply, in situ, the addition product formed being readily crystallizable.

To summarize, all the present methods of synthesis have major disadvantages which make them difficult, if not impossible, to adapt to the industrial scale.

Thus, the direct formation of methylidene-malonate cannot be used because it leads to inevitable polymerization of the methylidenemalonate formed.

In cases where an intermediate addition product is prepared, this is often difficult to filter off and purify by recrystallization and is always contaminated by considerable quantities of conjugated dienes used for the Diels-Alder reaction, this contamination affecting the subsequent thermolysis or hydrolysis step. In the processes of the prior art, purification by distillation under a high vacuum is therefore necessary in this case.

In addition, the yields are generally relatively modest and the number of steps required to form methylidenemalonate is relatively large, especially in the case where asymmetrical esters are formed.

The object of the present invention is therefore to solve the new technical problem of providing a new process for the synthesis of methylidenemalonate which can be used on the industrial scale, is very simple and reliable, uses inexpensive reactants, has a minimum number of steps, preferably only two main steps, gives products of high purity in high yields and makes it possible to prepare a wide range of products, including those carrying reactive groups on the above-mentioned ester substituents $R^1$ and $R^2$.

Another main object of the present invention is to solve the new technical problem of forming assymmetrical methylidenemalonates and in particular those in which one of the esters has been substituted by at least one functional group such as ether, epoxide, halogen, cyano, ester, aldehyde, ketone, aryl etc.

Preferably, one of the ester is for instance $R^2$ of the formula $-(CH_2)_n-COOR'$, wherein $R'$ is a lower alkyl having from 1 to 5 carbon atoms and n is an integer from 1 to 5 inclusive.

Another object of the present invention is to solve the new technical problem of providing a new process for the synthesis of methylidenemalonate by the formation of an addition product or adduct of the Diels-Alder type very simply and very rapidly, in a high yield, this addition compound advantageously being capable of undergoing hemihydrolysis—which was previously impossible—enabling asymmetrical addition products to be prepared, as desired, by alkylation with an appropriate halide, thereby allowing synthesis of asymmetrical methylidenemalonate esters among which one of the esters if of the formula $-(CH_2)_n-COOR'$, wherein $R'$ is a lower alkyl having from 1 to 5 carbon atoms and n is an integer from 1 to 5 inclusive.

Another object of the present invention is to solve the new technical problem of forming novel intermediate addition products which can be used for the synthesis of methylidenemalonate and are capable of being isolated easily by crystallization, with a high purity, whereby small amounts of contaminants in no way affect their ability to form methylidenemalonates in a subsequent step, these addition products being symmetrical or, advantageously, asymmetrical esters or monoesters.

Preferably, these addition products enable methylidenemalonate to be obtained by thermolysis at considerably lower temperatures than in the case of other known addition products.

Moreover, the invention also provides a solution which uses solvents of low toxicity to facilitate the extraction and isolation of the addition products.

All these new technical problems are solved for the first time by the present invention, very simply and rapidly, with the formation of addition products and methylidenemalonate with a high purity and in high yields.

Thus, according to a first aspect, the present invention provides a process for the preparation of monoesters or diesters of 9,10-endoethano-9,10-dihydroanthracene-11,11-dicarboxylic acid of the following formula (II):

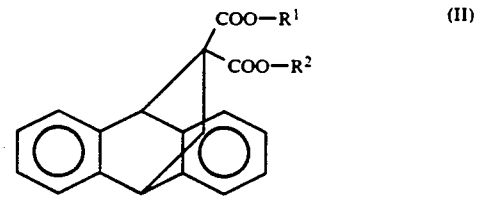

in which $R^1$ and $R^2$ can be identical or different and can represent H, an alkali metal or alkaline earth metal atom, especially sodium or potassium, a linear or branched alkyl group having from 1 to 6 carbon atoms, an alicyclic group having from 3 to 6 carbon atoms, an alkenyl group having from 2 to 6 carbon atoms, defined in their cis or trans variety, or an alkynyl group having from 2 to 6 carbon atoms, the said groups optionally being substituted by one or more functional groups such as ether, epoxide, halogeno, cyano, ester, aldehyde, ketone, aryl etc., where $R^1$ and $R^2$ cannot be H simultaneously, which comprise reacting a corresponding malonic acid ester with formaldehyde, in the presence of anthracene, so as to give the said monoester or diester in the form of an addition product, and preferably separating this monoester or diester from the reaction medium so that it can be obtained, advantageously, in the form of a crystalline product. Preferred compounds of formula (II) are those wherein $R^1$ is a lower alkyl form 1 to 5 carbon atoms and $R^2$ is a radical of the formula $-(CH_2)_n-COOR'$, wherein $R'$ is a lower alkyl from 1 to 5 carbon atoms and n is an integer from 1 to 5, said radical $R^2$ being obtained by a reaction of ester exchange.

In an advantageous embodiment of this process, the reaction takes place in a non-aqueous solvent medium in the presence of a catalyst which is preferably selected from copper(II) acetate, potassium acetate and mixtures thereof.

Advantageously, this non-aqueous solvent is selected from a water-immiscible solvent and, advantageously, a water-miscible solvent. The following may be mentioned among these solvents: acetic acid, acetic anhydride, benzene, bromobenzene, xylene, toluene, dimethylformamide (DMF), dimethyl sulfoxide (DMSO), a ketone such as dimethyl ketone or ethyl methyl ketone, acetonitrile, dioxane, N-methylpyrrolidone (NMP) or any mixture of at least 2 or 3 of these solvents.

In an advantageous embodiment, the monoester addition products are synthesized from the diester derivatives, preferably by reaction, in an alcoholic solvent, with an alkali metal or alkaline earth metal salt and especially sodium or potassium hydroxide.

In an equally advantageous embodiment, the asymmetrical diester addition products are prepared from the monoester addition product by reaction with a halogen-containing product whose radical is to form a second ester radical which is different from the first ester radical.

In an advantageous modified embodiment of the process, the reaction is carried out in a closed system, in particular in an autoclave or Carius tube.

According to a second aspect, the present invention also provides novel monoesters and diesters of 9,10-endoethano-9,10-dihydroanthracene-11,11-dicarboxylic acid which advantageously correspond to the following structural chemical formula (II):

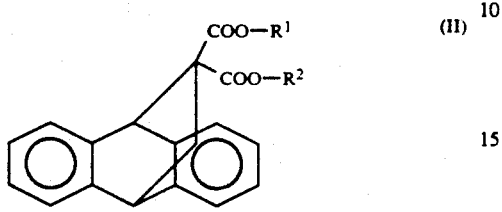

in which $R_1$ and $R_2$ can be identical or different and can represent H, an alkali metal or alkaline earth metal atom, especially sodium or potassium, a linear or branched alkyl group having from 1 to 6 carbon atoms, an alicyclic group having from 3 to 6 carbon atoms, an alkenyl group having from 2 to 6 carbon atoms, defined in their cis or trans variety, or an alkynyl group having from 2 to 6 carbon atoms, the said groups optionally being substituted by one or more functional groups such as ether, epoxide, halogeno, cyano, ester, aldehyde, ketone, aryl etc., whereby $R^1$ and $R^2$ cannot be H or an ethyl group simultaneously. Preferred compounds of formula (II) are those wherein $R^1$ is a lower alkyl from 1 to 5 carbon atoms and $R^2$ is a radical of the formula —COO(CH$_2$)$_n$—COOR', wherein R' is a lower alkyl having from 1 to 5 carbon atoms and n is an integer from 1 to 5 inclusive. These asymmetrical esters represent a new class of compounds, which allows to prepare a corresponding new class of asymmetrical methylidenemalonates of hereinabove defined formula (Ia).

Particular, the invention includes the following monoesters and diesters, which constitute intermediate addition products for the preparation of methylidenemalonates:

- 11,11-di-n-propoxycarbonyl-9,10-endoethano-9,10-dihydroanthracene,
- 11,11-di-n-butoxycarbonyl-9,10-endoethano-9,10-dihydroanthracene,
- 11-n-butoxycarbonyl-11-n-pentoxycarbonyl-9,10-endoethano-9,10-dihydroanthracene,
- 11-ethoxycarbonyl-11-ethoxycarbonylmethyleneoxycarbonyl 9,10-endoethano-9,10-dihydroanthracene,
- 11,11-dimethoxycarbonyl-9,10-endoethano-9,10-dihydroanthracene,
- 11-methoxycarbonyl-11-n-butoxycarbonyl-9,10-endoethano-9,10-dihydroanthracene,
- 11-methoxycarbonyl-11-n-hexyloxycarbonyl-9,10-endoethane-9,10-dihydroanthracene,
- 11-methoxycarbonyl-11-benzyloxycarbonyl-9,10-endoethano-9,10-dihydroanthracene,
- 11,11-diethoxycarbonyl-9,10-endoethano-9,10-dihydroanthracene,
- 11-ethoxycarbonyl-11-n-propoxycarbonyl-9,10-endoethano-9,10-dihydroanthracene,
- 11-ethoxycarbonyl-11-n-butoxycarbonyl-9,10-endoethano-9,10-dihydroanthracene,
- 11-ethoxycarbonyl-11-allyloxycarbonyl-9,10-endoethano-9,10-dihydroanthracene,
- 11-ethoxycarbonyl-11-prop-3-ynyloxycarbonyl-9,10-endoethano-9,10-dihydroanthracene,
- 11-ethoxycarbonyl-11-methoxymethoxycarbonyl-9,10-endoethano-9,10-dihydroanthracene,
- 11-ethoxycarbonyl-11-ethoxyethoxycarbonyl-9,10-endoethano-9,10-dihydroanthracene,
- 11-ethoxycarbonyl-11-ethoxycarbonyl propyleneoxycarbonyl 9,10-endoethano-9,10-dihydroanthracene,
- 11-ethoxycarbonyl-11-(2',3'-epoxypropoxycarbonyl)-9,10-endoethano-9,10-dihydroanthracene,
- 11-ethoxycarbonyl-11-propan-3-olyloxycarbonyl-9,10-endoethano-9,10-dihydroanthracene,
- 11-n-propoxycarbonyl-11-n-butoxycarbonyl-9,10-endoethano-9,10-dihydroanthracene,
- 11,11-diisopropoxycarbonyl-9,10-endoethano-9,10-dihydroanthracene,
- 11,11-diisobutoxycarbonyl-9,10-endoethano-9,10-dihydroanthracene,
- 11,11-di-n-pentoxycarbonyl-9,10-endoethano-9,10-dihydroanthracene,
- 11,11-diallyloxycarbonyl-9,10-endoethano-9,10-dihydroanthracene
- 11,11-trimethylidene-1',3'-dioxycarbonyl-9,10-endoethano-9,10-dihydroanthracene, and
- 11-methoxycarbonyl-1-methoxycarbonyl methylene oxycarbonyl-910-endoethano-9,10-dihydroanthracene.

Finally, according to a third aspect, the invention also includes the use of the monoesters or diesters for the preparation of methylidenemalonates by any treatment known per se, such as a heat treatment, thermolysis, pyrolysis or else hydrolysis.

The general chemical process for preparing the asymmetrical esters is given in attached scheme 3.

Other objects, characteristics and advantages of the invention will become clearly apparent from the following explanatory description, which gives a few preparative examples simply by way of illustration and hence without in any way limiting the scope of the invention.

EXAMPLE 1

Preparation of 11,11-diisopropoxycarbonyl-9,10-endoethano-9,10-dihydroanthracene (II, $R^1 = R^2 =$ iso-$C_3H_7$)

188 g (1 mol) of diisopropyl malonate are heated to 90°-100° C. by means of an oil bath, with stirring, in the presence of 60 g (2 mol) of paraformaldehyde, 178 g (1 mol) of anthracene, 10 g of copper (II) acetate and 10 g of potassium acetate in 500 ml of acetic acid and 500 ml of bromobenzene. The temperature is maintained at 90°-100° C. for 2 hours. The temperature of the oil bath is then raised gradually so as to distill initially an azeotropic mixture composed of water, bromobenzene and acetic acid and then the residual acetic acid. Distillation is stopped when the copper(II) and potassium acetates precipitate. The reaction medium is cooled to 60° C. and then poured into 1 l of toluene. This mixture is cooled to 10° C. and filtered on a Buchner funnel and the filtrate is evaporated to dryness. The solid residue is recrystallized from ethanol. The product obtained in this way has a purity of 94%; it is contaminated (6%) with anthracene. The product purified by chromatography on a column of silica gel (hexane/isopropanol: 95/5 v/v) has a melting point of 136°-7° C.; yield: 72%

(278.16 g). This compound analyzes correctly for the formula $C_{24}H_{26}O_4$.

EXAMPLE 2

Preparation of 11,11-diallyloxycarbonyl-9,10-endoethano-9,10-dihydroanthracene (II, $R^1=R^2=CH_2-CH=CH_2$)

The procedure is the same as in Example 1 but the following amounts of reactants are used: 46 g (0.25 mol) of diallyl malonate, 15 g (0.5 mol) of paraformaldehyde, 44.5 g (0.25 mol) of anthracene, 5 g of copper (II) acetate and 5 g of potassium acetate in 120 ml of bromobenzene and 120 ml of acetic acid. After recrystallization, the product has a melting point of 85°-86° C. and the yield is 45% (41.35 g). This compound analyzes correctly for the formula $C_{24}H_{22}O_4$.

The following derivatives were also prepared by this process:

EXAMPLE 3bis

Synthesis of the potassium salt of 11-methoxycarbonyl-9,10-endoethano-9,10-dihydroanthracene-11-carboxylic acid (III, $R^1=CH_3$, $R^2=K$).

By starting from the first compound reported in the Table on page 14 for which $R^1=CH_3$ and $R^2=CH_3$, and by following the process described in example 3, it is obtained the title compound under the form of a potassium salt. (yield: 80%).

EXAMPLE 4

Synthesis of 11-allyloxycarbonyl-11-ethoxycarbonyl-9,10-endoethano-9,10-dihydroanthracene (II, $R^1=CH_2-CH=CH_2$, $R^2=C_2H_5$)

20 g (0.0555 mol) of (III) and 8.4 g (0.0555 mol) of

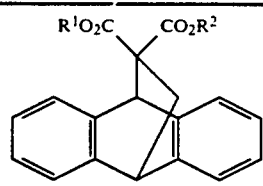

$R^1O_2C\quad CO_2R^2$

| $R^1$ | $R^2$ | Yield % | Melting point °C. | Elemental analysis |
|---|---|---|---|---|
| $CH_3$ | $CH_3$ | 53 | 161-162 | $C_{20}H_{18}O_4$ |
| $CH_3$ | $n-C_4H_9$ | 51 | 80-82 | — |
| $CH_3$ | $n-C_6H_{13}$ | 53 | 74-75 | — |
| $CH_3$ | $CH_2C_6H_5$ | 42 | 109-112 | — |
| $C_2H_5$ | $C_2H_5$ | 75 | 130-131 | $C_{22}H_{22}O_4$ |
| $C_2H_5$ | $n-C_3H_7$ | 82 | 107-108 | $C_{23}H_{24}O_4$ |
| $C_2H_5$ | $n-C_4H_9$ | 46 | 91-92 | — |
| $C_2H_5$ | $CH_2-CH=CH_2$ | 84 | 88-89 | $C_{22}H_{22}O_4$ |
| $C_2H_5$ | $CH_2-C\equiv CH$ | 62 | 60-61 | — |
| $C_2H_5$ | $CH_2OCH_3$ | 75 | 106-107 | $C_{22}H_{22}O_5$ |
| $C_2H_5$ | $C_2H_4OC_2H_5$ | 47 | 42-46 | — |
| $C_2H_5$ | $CH_2CO_2C_2H_5$ | 42 | 76-77 | — |
| $C_2H_5$ | $(CH_2)_3CO_2C_2H_5$ | 67 | 83-84 | — |
| $C_2H_5$ | $CH_2CH\underset{O}{\overset{\diagup\diagdown}{\text{———}}}CH_2$ | 66 | 114-115 | $C_{23}H_{22}O_5$ |
| $C_2H_5$ | $CH_2CH_2CH_2-OH$ | 53 | 95-98 | — |
| $n-C_3H_7$ | $n-C_3H_7$ | 72 | 104-106 | $C_{24}H_{26}O_4$ |
| $n-C_3H_7$ | $n-C_4H_9$ | 47 | 91-92 | — |
| $iso-C_3H_7$ | $iso-C_3H_7$ | 72 | 136-137 | $C_{24}H_{26}O_4$ |
| $n-C_4H_9$ | $n-C_4H_9$ | 55 | 91-92 | $C_{26}H_{30}O_4$ |
| $iso-C_4H_9$ | $iso-C_4H_9$ | 52 | 94-95 | $C_{26}H_{30}O_4$ |
| $n-C_4H_9$ | $n-C_5H_{11}$ | 53 | 77-79 | — |
| $n-C_5H_{11}$ | $n-C_5H_{11}$ | 45 | 75-76 | — |
| $CH_2CH=CH_2$ | $CH_2CH=CH_2$ | 41 | 85-86 | — |
| $-CH_2-CH_2-CH_2-$ | | 53 | 115-118 | — |

EXAMPLE 3

Synthesis of the potassium salt of 11-ethoxycarbonyl-9,10-endoethano-9,10-dihydroanthracene-11-carboxylic acid (III, $R^1=C_2H_5$, $R^2=K$)

A solution of 18.6 g (0.324 mol) of potassium hydroxide in 400 ml of absolute ethanol is added dropwise, with stirring, to a solution of 100 g (0.286 mol) of 11,11-diethoxycarbonyl-9,10-endoethano-9,10-dihydroanthracene in 400 ml of absolute ethanol, heated to 65° C. After 4 hours, the reaction mixture is cooled to ordinary temperature and the potassium salt which has precipitated is filtered off and washed with diethyl ether. After drying in vacuo at ordinary temperature, 92 g (yield: 90%) of a white powder are obtained.

allyl bromide are reacted in 250 ml of anhydrous dimethylformamide. The reaction medium is heated to 80° C., stirred for 2 hours, diluted in 2 l of water and filtered; the precipitate is washed with water and recrystallized from ethanol to give 17 g (85%) of a product with a melting point of 88°-89° C. This compound analyzes correctly for the formula $C_{23}H_{22}O_4$.

EXAMPLE 4bis

Synthesis of 11-methoxycarbonyl, 11-methoxycarbonyl methylene oxycarbonyl-9,10-endoethano-9,10-dihydroanthracene (II, $R^1=-CH_3$, $R^2=-CH_2COOCH_3$.

By starting from the compound obtained in example 3bis, by reacting it with methylbromoacetate of formula BrCH₂COOMe, it is obtained the title compound having a melting point of 116°-117° C. (yield: 75%).

EXAMPLE 5

Synthesis of 11-(2',3'-epoxypropoxycarbonyl)-11-ethoxycarbonyl-9,10-endoethano-9,10-dihydroanthracene (II,

$R^1 = CH_2—CH—CH_2—O, R^2 = C_2H_5$)

The procedure is the same as in Example 4 but the following amounts of reactants are used: 20 g (0.0555 mol) of (III) and 8.9 g (0.065 mol) of epibromohydrin. The product is obtained with a yield of 70% after recrystallization from ethanol (melting point: 114°-115° C.). This compound analyzes correctly for the formula $C_{23}H_{22}O_5$.

EXAMPLE 6

Synthesis of 11,11-trimethylene-1',3'-dioxycarbonyl-9,10-endoethano-9,10-dihydroanthracene (II, $R^1R^2=—CH_2—CH_2—CH_2—$)

5 g (0.013 mol) of 11-ethoxycarbonyl-11-propan-3-olyloxycarbonyl-9,10-endoethano-9,10-dihydroanthracene (II, $R^1=C_2H_5$, $R^2=—C_2H_4—CH_2OH$), obtained by alkylation of the potassium salt (III, $R^1=C_2H_5$, $R^2=K$) with 3-bromopropan-1-ol in DMF, are reacted in 50 ml of xylene (dry) with a catalytic amount of NaH (60% dispersion in paraffin oil). A vigreux column is fitted to the top of the round-bottomed flask and the mixture is heated so as to distill the xylene/ethanol azeotrope. After evaporation of the solvent, the solid residue is recrystallized from ethanol.

Yield: 53% (2.52 g); melting point: 115°-118° C.

Examples 7 to 10 below relate to advantageous modified embodiments of the basic process for the preparation of the addition product (II).

EXAMPLE 7

Use of xylene in place of bromobenzene
This reduces the cost and the toxicity.
Amount of solvent:
  1.5 volumes of xylene
  1 volume of acetic acid The other conditions are identical to those described for bromobenzene to Example 1 but di-n-butyl malonate is used as the starting material in place of diisopropyl malonate.

11,11-Di-n-butoxycarbonyl-9,10-endoethano-9,10-dihydroanthracene (II, $R^1=R^2=n—C_4H_9$) is obtained; yield: 55%, melting point: 91°-92° C.

EXAMPLE 8

Use of a water-miscible solvent
The method of isolation is easier.

A range of solvents which ensured thermal conditions similar to the xylene (or bromobenzene) process but were water-miscible was studied. The distillation of high-boiling solvents is thus avoided, the reaction product being isolated by filtration after the addition of water.

The reaction mixture is cooled after being heated for 3 hours at 140° C. This mixture is poured into water and the solid is filtered off. The remainder of the process is identical to that of Example 1.

The yields given in the table are those obtained for the synthesis of 11,11-diethoxycarbonyl-9,10-endoethano-9,10-dihydroanthracene (II, $R^1=R^2=C_2H_5$) from diethyl malonate.

| Solvents (proportions v/v) | Yield % |
| --- | --- |
| DMF/acetic acid/C₆H₆ 9 9 2 | 24 |
| DMSO/acetic acid 1 1 | 8 |
| DMSO/acetic acid/dioxane 2 0.8 2 | 25 |
| DMSO/acetic acid/toluene 2 1 2 | 28 |
| NMP/acetic acid/xylene 2 2 0.8 | 51 |

EXAMPLE 9

Use of an autoclave or a Carius tube
Closed-system process

Example: synthesis of 11,11-diethoxycarbonyl-9,10-endoethano-9,10-dihydroanthracene An autoclave (capacity: 100 ml) is charged with 17 g of anthracene, 6 g of paraformaldehyde and 16 g of diethyl malonate.

The catalyst is a mixture of 0.5 g of cupric acetate and 0.5 g of potassium acetate.

The solvent (50 ml) is a mixture of acetic acid and benzene in the ration 2.5/7.5 (v.v).

The autoclave is closed and then immersed for 2 hours in an oil bath heated to 90°-100° C. The temperature of the bath is raised gradually to 140°-150° C. over a period of 3 hours. The autoclave is cooled to room temperature and then opened. The reaction mixture is taken up with 100 ml of benzene. CaCl₂ (anhydrous) is added to the solution. After filtration, the solvents are evaporated off and the solid residue is recrystallized from ethanol. Yield: 67%; melting point: 127°-129° C.

The following table shows the different conditions examined. The amount of reactants are identical to those described in the above example (unless indicated otherwise).

| Solvents (proportions v/v) | Catalyst | Yield |
| --- | --- | --- |
| xylene/acetic acid 1 1 | (Ac)₂Cu + AcK | 62% |
| benzene/acetic acid 1 1 | " | 41% |
| benzene/acetic acid 7/8 1/8 | " | 49% |
| benzene/acetic acid 15/16 1/16 | " | 46% |
| benzene/acetic acid 3/4 1/4 | " | 67% |
| benzene/acetic acid 3/4 1/4 (heating for 12 h) | " | 46% |
| xylene/acetic acid/acetic anhydride 2 2 1 | " | 32% |
| xylene/acetic anhydride 2 1 | " | 32% |
| dimethyl ketone/acetic acid 3/4 1/4 | " | 56% |
| ethyl methyl ketone/acetic acid 3/4 1/4 | " | 63% |
| acetonitrile/acetic acid 3/4 1/4 | " | 58% |
| dioxane/acetic acid 3/4 1/4 | " | 56% |
| dioxane/acetic acid 3/4 1/4 | (ClCH₂CO₂)₂Mg 1 g | 31% |
| dimethyl ketone/acetic acid 3/4 1/4 | (ClCH₂CO₂)₂Mg 1 g | 26% |
| xylene/acetic acid/acetic anhydride | (ClCH₂CO₂)₂Mg | 56% |

-continued

| Solvents (proportions v/v) | | Catalyst | Yield |
|---|---|---|---|
| 5 | 2 | 1 g | |
| benzene/acetic acid | | $(ClCH_2CO_2)_2Mg$ | 60% |
| 3/4 | 1/4 | 1 g + $(Ac)_2Cu$ | |
| | | 0.5 g + AcK 0.5 g | |
| methyl ethyl ketone/acetic acid | | $(Ac)_2Cu$ | 75% |
| 3/4 | 1/4 | 2.5 g | |

EXAMPLE 10

Synthesis of 1,1-diisopropoxycarbonylethene (I, $R^1=R^2=$iso-$C_3H_7$)

50 g (0.132 mol) of the adduct described in Example 1 and 10.37 g (0.105 mol) of maleic anhydride are dispersed in 250 ml of mineral oil, with thorough stirring and under a stream of dry nitrogen. This suspension is heated gradually to 200°-220° C. This temperature is maintained for 45 minutes, after which the reaction mixture is cooled to ordinary temperature, placed under a vacuum (0.1 Torr) and distilled. The fraction boiling at 40° C. is collected. Yield: 64% (16.89 g). Purity: 99% (contaminant: 1% of maleic anhydride). Mass spectrum (70 eV), chemical ionization (isobutane): 201 (M+1), 159, 117.

EXAMPLE 10bis

Synthesis of 1-methoxycarbonyl-1-methoxycarbonyl methylene oxycarbonyl ethene (I, $R^1=CH_3$, $R^2=-CH_2COOCH_3$).

The procedure is the same as that described in example 10, but the reactants used are the adduct of example 4bis and maleic anhydride in mineral oil. The product obtained after distillation under 0.05 Torr has a boiling point of 100° C., and the yield is of 40%.

EXAMPLE 11

Synthesis of 1-allyloxycarbonyl-1-ethoxycarbonylethene (I, $R^1=C_2H_5$, $R^2=CH_2-CH=CH_2$)

The procedure is the same as that described in Example 10 but the reactants used are 10 g (0.0276 mol) of the adduct of Example 4 and 2.16 g (0.022 mol) of maleic anhydride in 70 ml of mineral oil. The product obtained after distillation under 0.25 Torr has a boiling point of 53° C., the yield is 48% (2.4 g) and the purity is 99% (contaminant: 1% of maleic anhydride).

Examples 10 and 11 are representative of the general method for the thermolysis of the adducts (II) in the presence of maleic anhydride.

The following are examples of compounds which can be prepared by the method:

$$H_2C=C\begin{array}{c}CO_2R^1\\CO_2R^2\end{array}$$

| $R^1$ | $R^2$ | Yield % | Boiling Point °C. (Torr) |
|---|---|---|---|
| $CH_3$ | $CH_3$ | 54 | 80-82 (6) |
| $CH_3$ | n-$C_4H_9$ | 75 | 65-68 (0.4) |
| $CH_3$ | n-$C_6H_{13}$ | 77 | 80-85 (0.1) |
| $C_2H_5$ | $C_2H_5$ | 67 | 60-61 (0.25) |
| $C_2H_5$ | $C_3H_7$ | 63 | 52-55 (0.3) |
| $C_2H_5$ | $C_4H_9$ | 71 | 62-63 (0.2) |
| $C_2H_5$ | $CH_2-CH=CH_2$ | 48 | 53-55 (0.25) |
| $C_2H_5$ | $CH_2-C\equiv CH$ | 20 | 65-77 (0.3) |
| $C_2H_5$ | $C_2H_4OC_2H_5$ | 43 | 82-84 (0.2) |
| $C_2H_5$ | $CH_2CO_2C_2H_5$ | 62 | 98-99 (0.1) |
| $C_2H_5$ | $CH_2CH_2CH_2CO_2C_2H_5$ | 32 | 86-89 (0.06) |
| n-$C_3H_7$ | n-$C_3H_7$ | 81 | 77-78 (0.2) |
| n-$C_3H_7$ | n-$C_4H_9$ | 54 | 78-80 (0.1) |
| iso-$C_3H_7$ | iso-$C_3H_7$ | 64 | 40-42 (0.1) |
| n-$C_4H_9$ | n-$C_4H_9$ | 68 | 76-80 (0.01) |
| n-$C_4H_9$ | n-$C_5H_{11}$ | 78 | 95-96 (0.1) |
| n-$C_5H_{11}$ | n-$C_5H_{11}$ | 46 | 99-101 (0.05) |
| isobutyl | isobutyl | 61 | 64-65 (0.02) |
| allyl | allyl | 48 | 67-68 (0.3) |

Thus it is seen that the present invention makes it possible to prepare addition products with anthracene very simply and very rapidly, with a high purity and also in high yields. Moreover, it is possible to prepare asymmetrical addition products as the basic addition products can undergo hemihydrolysis in a basic medium to give an alkali metal or alkaline earth metal monosalt of an 11-alkoxycarbonyl-9,10-endoethano-9,10-dihydroanthracene-11-carboxylic acid, which, on alkylation with an appropriate halide $R^3-X$ in dimethylformamide, yields the asymmetrical addition product in accordance with the attached schemes 2 and 3.

Thus, the asymmetrial addition product, treated at about 220° C. in a mineral oil, in the presence of maleic anhydride, or by any other means of thermolysis or pyrolysis, yields the corresponding olefin, i.e. the corresponding methylidenemalonate.

The process according to the invention thus makes it possible to prepare methylidenemalonates from malonate esters in two essential steps, namely, in a first step, the reaction of the malonic acid ester with formaldehyde in the presence of anthracene, in accordance with scheme 1 below, and, in a second step, the heat treatment of the addition product obtained in the first step to form the corresponding methylidenemalonate, this advantageously taking place in the presence of maleic anhydride so as to separate out the anthracene in the form of another addition product (scheme 1).

The present invention therefore includes all the means which constitute technical equivalents of the means described and claimed in the claims.

SCHEME: 1

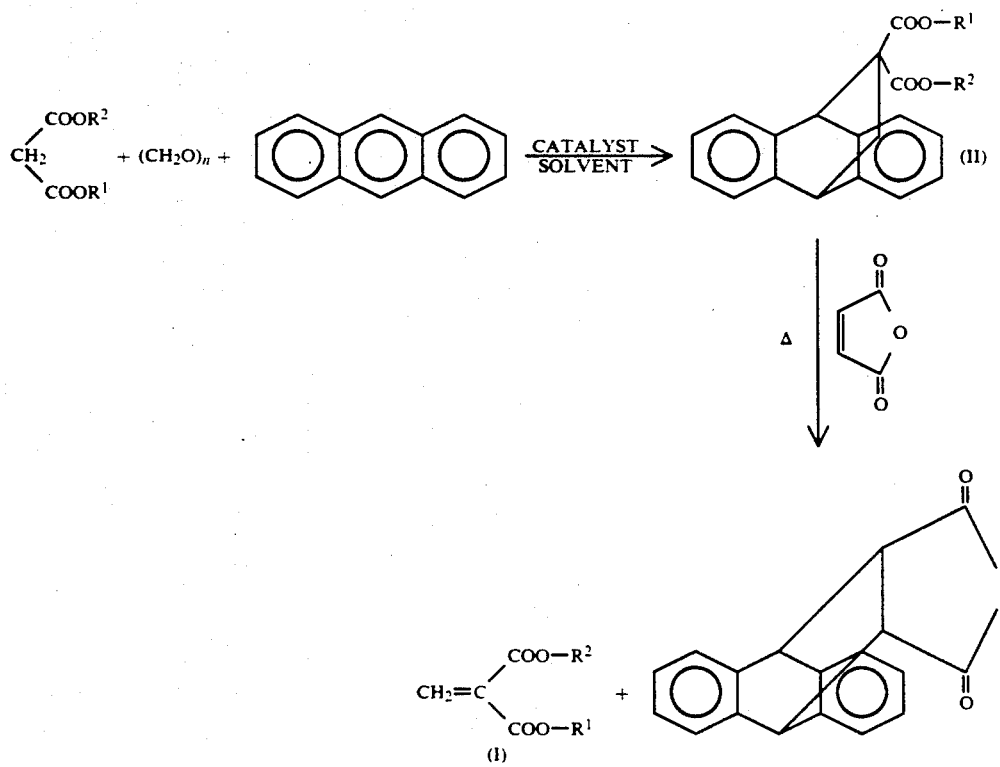
SCHEME: 2
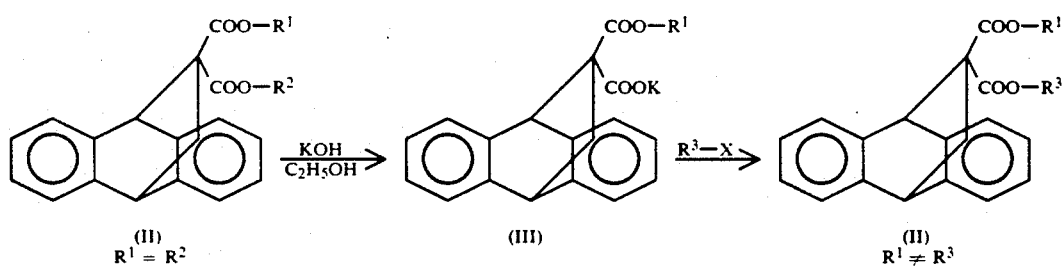
SCHEME: 3
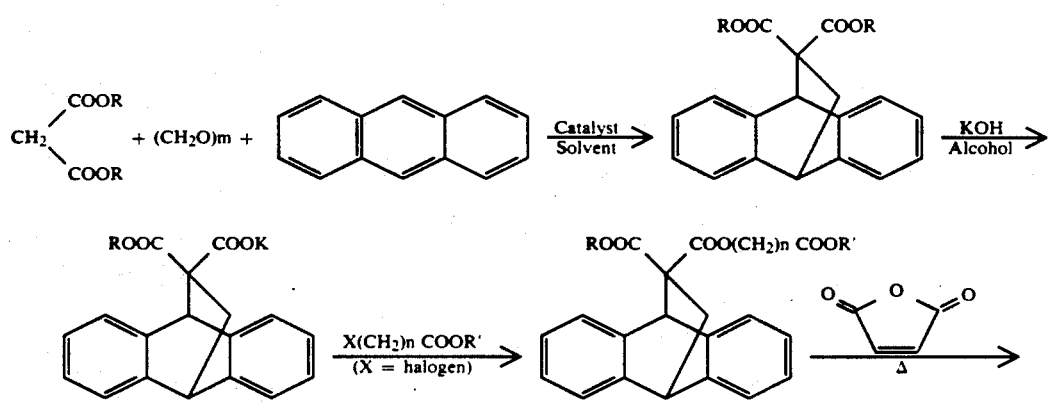

-continued

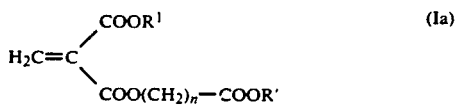 + 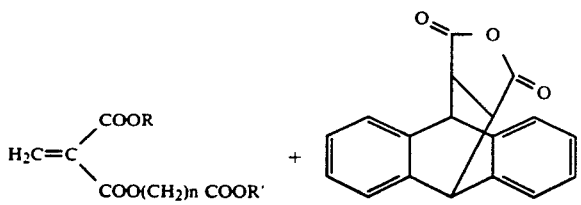

What is claimed is:

1. An asymmetrical methylidenemalonate diester of the following structural chemical formula (Ia):

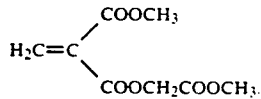 (Ia)

wherein $R^1$ and $R'$ each represent a lower alkyl having from 1 to 5 carbon atoms, and n is an integer from 1 to 5 inclusive.

2. An asymmetrical methylidenemalonate diester of the following structural chemical formula:

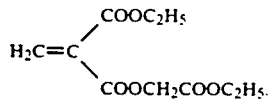

3. An asymmetrical methylidenemalonate diester of formula:

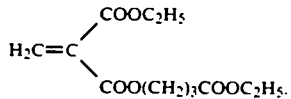

4. An asymmetrical methylidenemalonate diester of formula:

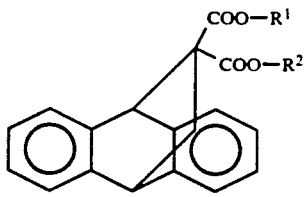

5. A 9,10-endoethano-9,10-dihydroanthracene-11,11-dicarboxylic acid derivative, having the following structural formula (II):

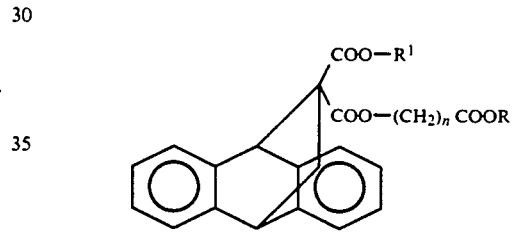 (II)

in which $R^1$ and $R^2$ can be identical or different and can represent H, and alkali metal or alkaline earth metal atom, a linear or branched alkyl group having from 1 to 6 carbon atoms, an alicyclic group having from 3 to 6 carbon atoms, an alkenyl group having from 2 to 6 carbon atoms, defined in their cis or trans variety, or an alkynyl group having from 2 to 6 carbon atoms, where $R^1$ and $R^2$ cannot be H or ethyl simultaneously.

6. A derivative as defined in claim 5, wherein the $R^1$ and $R^2$ groups are substituted by a functional group selected from the group consisting of ether, epoxide, and ester.

7. A derivative as defined in claim 5, wherein $R^1$ or $R^2$ can be sodium or potassium.

8. A 9,10-endoethano-9,10-dihydroanthracene-11,11-dicarboxylic acid derivative having —COO—$R^3$ and —COO—$R^4$ substituents at the 11 position in which $R^3$ and $R^4$ are identical and represent a methyl, n-propyl, n-butyl or isobutyl, or are different and represent ethyl and methyleneoxymethyl or propyl.

9. A 9,10-endoethano-9,10-dihydroanthracene-11,11-dicarboxylic acid derivative, having the following structural chemical formula:

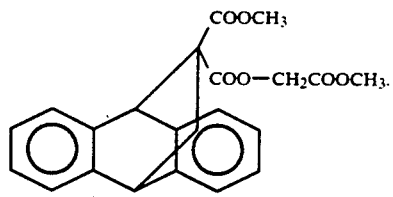

in which $R^1$ and $R'$ each represents a lower alkyl having from 1 to 5 carbon atoms, and n is an integer from 1 to 5, inclusive.

10. A 9,10-endoethano-9,10-dihydroanthracene-11,11-dicarboxylic acid derivative of the formula:

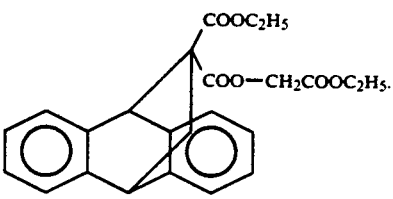

11. A 9,10-endoethano-9,10-dihydroanthracene-11,11-dicarboxylic acid derivative of the formula:

COOC$_2$H$_5$
COO—CH$_2$COOC$_2$H$_5$.

12. A 9,10-endoethano-9,10-dihydroanthracene-11,11-dicarboxylic acid derivative of the formula:

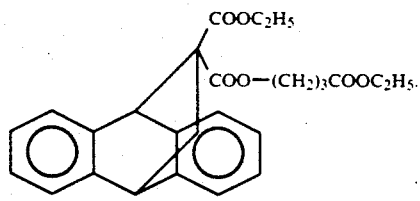

13. The compound selected from the group consisting of:
- 11,11-di-n-propoxycarbonyl-9,10-endoethano-9,10-dihydroanthracene,
- 11,11-d-n-butoxycarbonyl-9,10-endoethano-9,10-dihydroanthracen,
- 11-n-butoxycarbonyl-11-n-pentoxycarbonyl-9,10-endoethane-9,10-dihydroanthracene,
- 11-ethoxycarbonyl-11-ethoxycarbonylmethyleneoxycarbonyl-9,10-endoethano-9,10-dihydroanthracene,
- 11,11-dimethoxycarbonyl-9,10-endoethano-9,10-dihydroanthracene,
- 11-methoxycarbonyl-11-n-butoxycarbonyl-9,10-endoethano-9,10-dihydroanthracene,
- 11-methoxycarbonyl-11-n-hexyloxycarbonyl-9,10-endoethano-9,10-dihydroanthracene.
- 11-methoxycarbonyl-11-benzyloxycarbonyl-9,10-endoethano-9,10-dihydroanthracene,
- 11,11-diethoxycarbonyl-9,10-endoethano-9,10-dihydroanthracene,
- 11-ethoxycarbonyl-11-n-propoxycarbonyl-9,10-endoethano-9,10-dihydranthracene,
- 11-ethoxycarbonyl-11-n-butoxycarbonyl-9,10-endoethano-9,10-dihydroanthracene,
- 11-ethoxycarbonyl-11-allyloxycarbonyl-9,10-endoethano-9,10-dihydroanthracene,
- 11-ethoxycarbonyl-11-prop-2-ynyloxycarbonyl-9,10-endoethano-9,10-dihydroanthracene,
- 11-ethoxycarbonyl-11-methoxymethoxycarbonyl-9,10-endoethano-9,10-dihydroanthracene,
- 11-ethoxycarbonyl-11-ethoxyethoxycarbonyl-9,10-endoethano-9,10-dihydroanthracene,
- 11-ethoxycarbonyl-11-ethoxycarbonyl propyleneoxycarbonyl 9,10-endoethano-9,10-dichydroanthracene,
- 11-ethoxycarbonyl-11-(2',3'-epoxypropoxycarbonyl)-9,10-endoethano-9,10-dihydroanthracene,
- 11-ethoxycarbonyl-11-propane-3-olyloxycarbonyl-9,10-endoethano-9,10-dihydroanthracene,
- 11-n-propoxycarbonyl-22-n-butoxycarbonyl-9,20-endoethano-9,10-dihydroanthracene,
- 11,11-diisopropoxycarbonyl-9,10-endoethano-9,10-dihydroanthracene,
- 11,11-diisobutoxycarbonyl-9,10-endoethano-9,10-dihydroanthracene,
- 11,11-di-n-pentoxycarbonyl-9,10-endoethano-9,10-dihydroanthracene,
- 11,11-diallyloxycarbonyl-9,10-endoethano-9,10-dihydroanthracene,
- 11,11-trimethylidene-1',3'-dioxycarbonyl-9,10-endoethano-9,10-dihydroanthracene, and
- 11-methoxycarbonyl-11-methoxycarbonyl methylene oxycarbonyl-9,10-endoethane-9,10-dihydroanthracene.

* * * * *